(12) United States Patent
Zaouali et al.

(10) Patent No.: US 6,574,508 B2
(45) Date of Patent: Jun. 3, 2003

(54) DISMOUNTABLE CONNECTOR HEAD FOR AN ACTIVE IMPLANTABLE MEDICAL DEVICE SUCH AS A PACEMAKER, A DEFIBRILLATOR AND/OR CARDIOVERTOR

(75) Inventors: Mounir Zaouali, Paris (FR); Philippe Correas, Soissy sous Montmorency (FR); Philippe D'Hiver, Chatillon (FR)

(73) Assignee: Ela Medical S.A., Montrouge (FR)

( * ) Notice: Subject to any disclaimer, the term of this patent is extended or adjusted under 35 U.S.C. 154(b) by 0 days.

(21) Appl. No.: 09/919,983

(22) Filed: Jul. 31, 2001

(65) Prior Publication Data

US 2002/0038136 A1 Mar. 28, 2002

(30) Foreign Application Priority Data

Jul. 31, 2000 (FR) .............................. 00 10069

(51) Int. Cl.$^7$ ................................. A61N 1/36
(52) U.S. Cl. ....................................... 607/36
(58) Field of Search ............................ 607/9, 36, 37

(56) References Cited

U.S. PATENT DOCUMENTS

| | | | |
|---|---|---|---|
| 4,182,345 A | 1/1980 | Grose | 128/419 |
| 5,775,743 A | 7/1998 | Rochelle | 607/37 |
| 5,851,221 A | 12/1998 | Rieder et al. | 607/93 |
| 5,919,215 A | 7/1999 | Wiklund et al. | 607/36 |

*Primary Examiner*—Scott M. Getzow
(74) *Attorney, Agent, or Firm*—Orrick, Herrington & Sutcliffe LLP

(57) ABSTRACT

A dismountable connector head for an active implantable medical device such as a pacemaker, defibrillator, and/or cardioverter. The device includes a case (12) comprising on one of its faces a series of emerging insulating traverse (16) structures bearing conducting feed-through leads (14), connected to the internal circuits of the case, and a connector head (10) made of an insulating rigid material, able to receive the terminals of electrical contact. A mechanical connection component (24) is used to solidarize the case with the connector head. The connection component is a removable component able to allow the separation (dismounting) of the connector head from the case after solidarisation of the two parts. The connection component can in particular be an elastically deformable clamp (24), cooperating by two opposed ends with a peripheral groove in the insulating traverses (16) bearing the conducting feed-through leads (14), or a pin similarly engaging a groove in the insulating traverse.

9 Claims, 3 Drawing Sheets

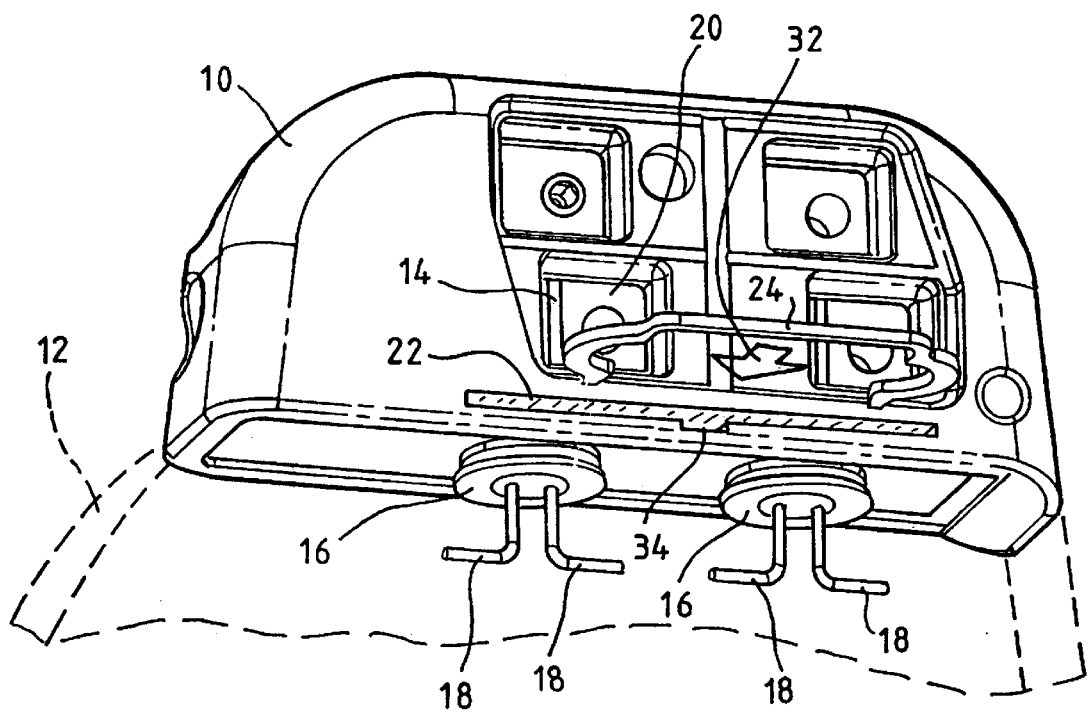
FIG_1
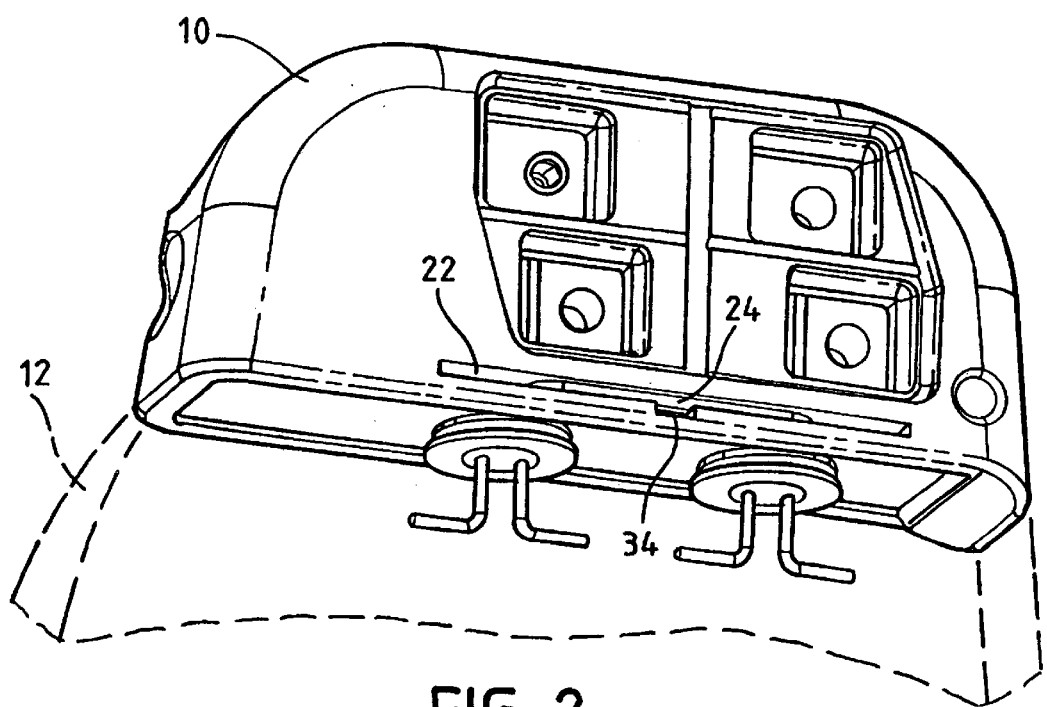
FIG_2

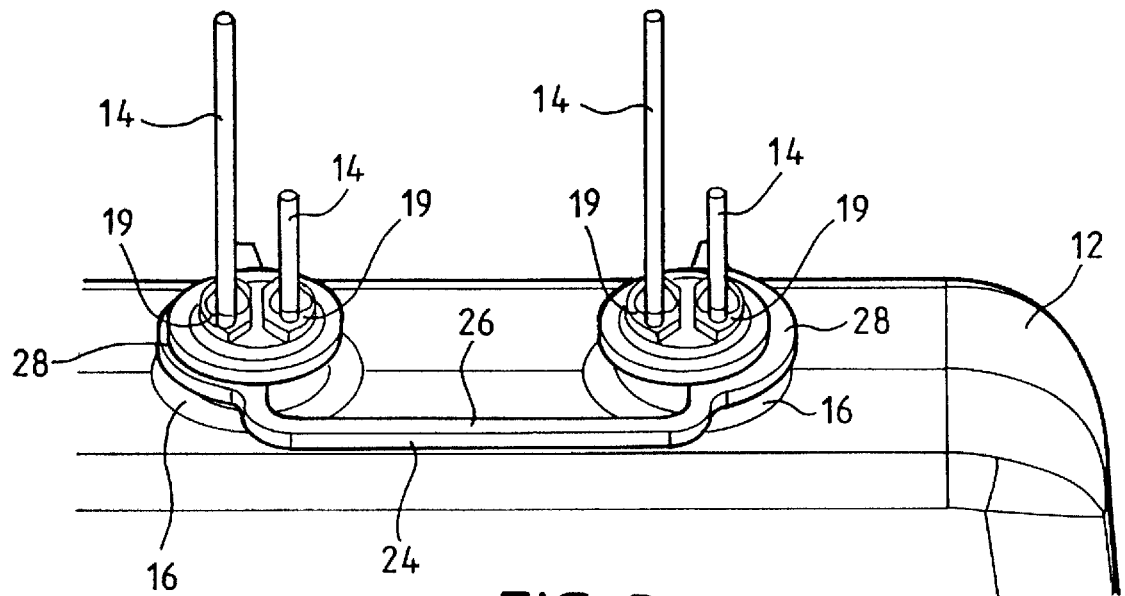
FIG_3
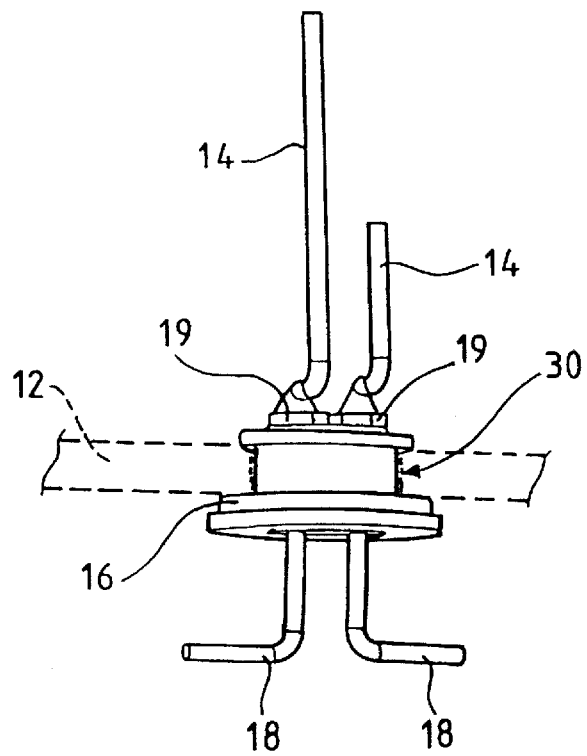
FIG_4

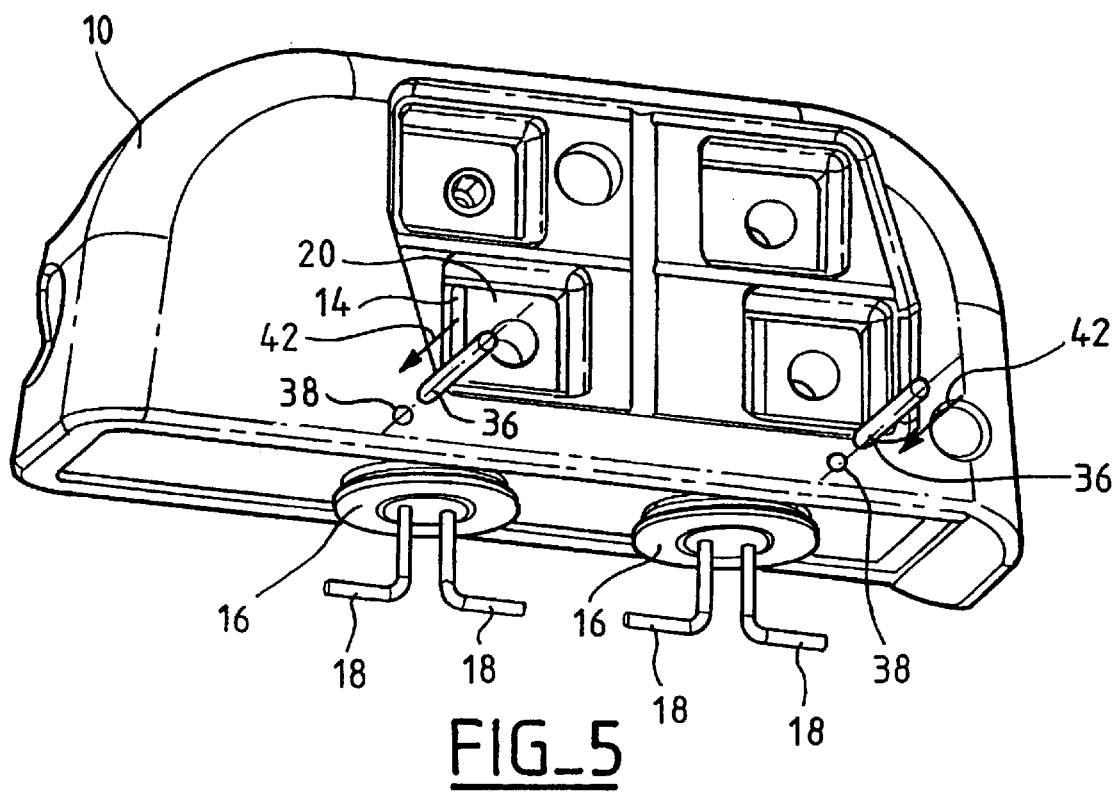
FIG_5
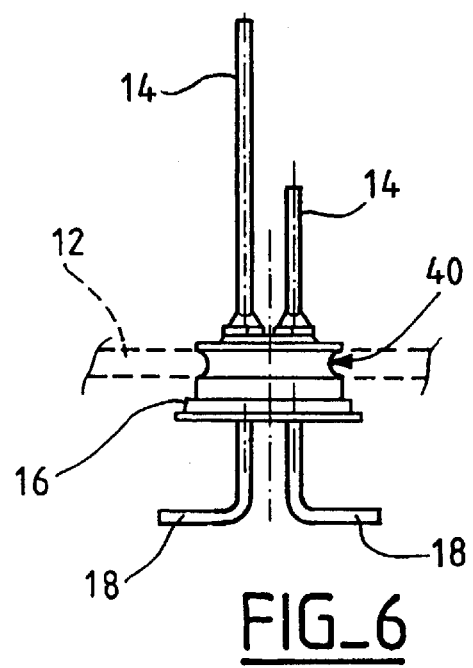
FIG_6

DISMOUNTABLE CONNECTOR HEAD FOR AN ACTIVE IMPLANTABLE MEDICAL DEVICE SUCH AS A PACEMAKER, A DEFIBRILLATOR AND/OR CARDIOVERTOR

FIELD OF THE INVENTION

The present invention relates to connectors, in particular connectors for active implantable medical devices.

Although the invention will be mainly described in the context of a pacemaker, it should be understood that this is only one exemplary embodiment of an invention that is applicable in a much more general way to a variety of "active implantable medical devices", as such devices are defined by the Jun. 20, 1990 Directive 90/385/CE of the Council of the European Communities. These devices include, in addition to pacemakers, and among other devices, defibrillators, cardiovertors, neurological apparatus, pumps for diffusion of medical substances, cochlear implants, and implanted biological sensors.

BACKGROUND OF THE INVENTION

Active implantable medical devices typically comprise a generator containing the electronics of the device that are connected electrically and mechanically to a probe, with the connection being realized by the surgeon at the time of the implantation. More specifically, the generator includes a case, containing the various electronic circuits and the power source of the device, and a connector head that is mechanically and electrically connected to the case. The connector head also is equipped with one or more cavities able to receive the probe(s).

The manufacture of the generator device generally comprises stages including initially, producing the complete case, containing the electronics and power source, the case having an upper face through which a plurality of feed-through leads are present. The feed-through leads are connected at one end to the electronic circuits within the case and are intended to be connected at one end to corresponding terminals of the connector head. The terminals in turn couple to the conductors of the external probe(s). The feed-through leads extend out through the face of the case in an "insulating traverse" structure, i.e., posts made of an insulating material that are fixed (e.g., welded) on the case.

Until now, the connector head has been generally assembled by connecting the various terminals to the corresponding feed-through leads, and then immersing the whole assembly in a molded silicone resin, ensuring at the same time the protection of the elements of the head, the sealing between head and case, and the definition of the cavities, coming from the molding, that are to receive the connecting (and conducting) extremities of the probes.

This technique of simultaneous assembly of all the elements of the head and of molding of the complete assembly is a proven and economic method, but it presents a certain number of disadvantages. One disadvantage is a lengthy time of manufacture, because it is necessary to await the complete drying of the silicone adhesive. Another disadvantage is a relatively larger volume needed for the connector head, because of the molding which comes to cover all the parts of the head. Yet another disadvantage exists in the event that a defect is discovered after the molding step, because it is impracticable, if not impossible, simply to separate the connector head from the case, isolate the defective part, and re-work the assembly.

Another manufacturing technique is known in which the connector head is made of a rigid material, for example, an epoxy resin or a polyurethane derivative such as Tecothane™. The case is then equipped with elastic claws with hooks that cooperate with homologous slits in the connector head, whose form allows a deployment of the claw hooks at the installation of the connector head to the case. This technique, although it makes it possible to reduce the time of manufacture, still presents the disadvantage of the impossibility of separating the connector head from the case once the generator assembly is made.

OBJECTS AND SUMMARY OF THE INVENTION

It is, therefore, an object of the present invention to provide a generator assembly including a connector head that has a reduced time of manufacture.

It is another advantage to provide a connector head that has a reduced volume.

It is yet another advantage to provide a connector head that has a possibility of separating the connector head from the case after assembly.

It is still another advantage to provide a connector head that has the possibility of controlling, piece by piece, the various elements of the operability of the structure of the connector.

It is another advantage to provide a connector head that has a reduced number of pieces necessary to allow the mechanical anchoring of the connector head.

To this end, the present invention proposes an active implantable medical device such as a pacemaker, a defibrillator and/or a cardiovertor, including: a case comprising a face through which a series of conducting feed-through leads emerge, the feed-through leads being connected to the internal circuits of the case; a connector head comprising a rigid insulating material, able to receive terminals of electrical contact; and a mechanical connection component, able to solidarize (interconnect) the case with the connector head, wherein the connection component is a removable component and on removal allows the separation of the connector head from the case after the initial solidarisation of the two parts.

Advantageously, the case also comprises at least one element able to cooperate with the connection component. This cooperating element is of a homologous form with that of the connection component at the point(s) of mutual contact. More preferably, the cooperating element is a surface feature or area, for example, a peripheral groove, in an insulating traverse carrying the conducting feed-through leads. Thus, the mechanical connection element is engaged with the connector head and the insulating traverse of the case, interconnecting the two elements together.

In a first embodiment, the mechanical connection component is an elastically deformable component able to cooperate with the aforementioned homologous cooperating element of the case by a click-and-ratchet mechanism, in particular, a clamp that is able to cooperate by two opposed ends with at least two insulating traverses of the case bearing the conducting feed-through leads. The clamp also cooperates with an aperture such as a slot in the connector head when engaged with the traverses to form the interconnection.

In a second embodiment, the mechanical connection component is a rigid component able to cooperate with the aforementioned homologous cooperating element of the case by an adjusted engagement, for example, a pin that is able to cooperate with an aperture such as a hole in the connector head, and a surface feature, such as a groove or an aperture in the insulating traverse of the case bearing the conducting feed-through leads.

BRIEF DESCRIPTION OF THE DRAWINGS

Other features, characteristics and advantages of the present invention will appear to a person of ordinary skill in the art, in view of the following detailed description, made with reference to the drawings annexed, in which the same reference characters refer to like elements, and in which:

FIG. 1 is a bottom perspective view of a connector head according to a first embodiment of the invention, before installation of a mechanical connection component;

FIG. 2 is identical to FIG. 1 after installation of the mechanical connection component;

FIG. 3 is a partial cut away view of the case of FIG. 2 illustrating the mechanical connection component cooperating with the insulating traverses emerging from the case of the device;

FIG. 4 is an isolated side view of an insulating traverse of FIG. 3;

FIG. 5 is a bottom perspective view of a connector head according to a second embodiment of the invention; and FIG. 6 is an isolated view of an insulating traverse of FIG. 5;

DETAILED DESCRIPTION OF THE DRAWINGS

With reference to FIGS. 1–6, reference 10 indicates in a general way a connector head according to the invention, manufactured in an insulating material, advantageously a rigid material such as an epoxy resin or a polyurethane derivative such as Tecothane. Thus, the invention contrasts with the known connector heads that are usually made out of a flexible material such as a silicone resin.

Head 10 is intended to be assembled on case 12 (shown in phantom lines) of an implantable active medical device such as, for example, a pacemaker, and hereinafter simply indicated "device" or "generator." This device thus includes a case 12 associated with head 10. Head 10 includes cavities into which the proximal extremities of one or more probes can be introduced, this connection being realized by the surgeon at the time of implantation.

Case 12 comprises a hollow metal shell, generally made of titanium, containing therein the electronics of the device and a power source (not shown). Case 12 has an open face out of which a series of feed-through leads 14 (see in particular FIG. 3) emerge via insulating traverses 16. Insulating traverses 16 are made of an insulating material 19 such as a ceramic.

Feed-through leads 14 are metal pins electrically connected to the inputs/outputs of the electronic circuits of the device, typically welded to these circuits at ends 18, which are, in addition, entirely enclosed in case 12 with the power source. The feed-through leads 14 emerge (FIG. 1) in corresponding cavities 20 of connector head 10 when the latter is assembled on case 12. These cavities 20 comprise the electric terminals for external probes (not represented). The cavities 20 then will be sealed closed by a closing cap (not represented), e.g., a silicon plug. The electric terminals are in particular terminals that are in conformity with the mechanical dimensional standard called "IS-1" of the French and European standard NF EN 50077 for a "Low Profile Connector For Implantable Pacemaker". This standard defines a connection system making it possible to guarantee the interchangeability of the probes and the pulse generators produced by various manufacturers. It will be understood however, that the invention is not limited to connection systems according to this standard, nor even to the connection systems suitable for pacemaker devices.

In the embodiment illustrated in FIGS. 1 to 4, the connector head 10 is provided at its bottom, i.e., in its area proximal to case 12, with an aperture 22 shaped to receive a mechanical connection component. In this embodiment, the mechanical connection component is a clamp 24, and the aperture 22 is a longitudinal slot 22 extending in a parallel plane in relation with the upper face of case 12. Slot 22 is homologous with elastic clamp 24, with slot 22 and clamp 24 being dimensioned so that the clamp 24 can be entirely introduced into slot 22, as illustrated in FIG. 2.

Clamp 24, as shown in more detail on FIG. 3, has a rectilinear central part 26, and two similar parts 28 at the extremities of part 26, such that parts 28 have a rounded form intended to come to retain themselves in respective homologous grooves 30 in insulating traverses 16 (see FIG. 4). In the illustrated embodiment, clamp 24 has a rectangular cross section, corresponding to the complementary shape of groove 30 in traverse 16. Other shaped sections (and grooves) could be used.

Clamp 24 is advantageously made out of a titanium alloy or a stainless steel, and its dimensions are selected according to the form and flexibility requirements, and to the respective positioning of insulating traverses 16, in a manner that it can be installed and retained astride on two traverses 16 by an elastic strain, in a reversible manner. Preferably, clamp 24 is constructed so that it can be installed by simple manual depression without the need of a particular tool.

The process of assembling connector head 10 onto case 12 is as follows. Case 12 presented, already assembled as a metal case having two insulating traverses 16 emerging, bearing feed-through leads 14, through an open face. Connector head 10 is then positioned on the corresponding face of the case with feed-through leads 14 disposed in cavities 20. The operator then inserts (arrow 32, FIG. 1) clamp 24 in slot 22 to engage and ratchet around the two insulting traverses 16, ensuring by this operation the mechanical solidarisation (interconnection) of head 10 and body 12. The resulting case-head unit or generator is presented in the form as illustrated in FIG. 2.

The generator unit formed by head 10 and the terminals (not represented) intended to be connected to each feed-through lead 14 emerging in cavities 20 (female terminals of the connection system) is assembled by welding each end of the feed-through leads 14 to its respective terminal.

In one alternate embodiment, it is possible to carry out the welding operation before the mechanical solidarisation of the head to the connector, but in this case a tool for positioning and supporting the head onto the body 12 is typically necessary.

The final stage is a stage of joining, namely sealing cavities 20 with a closing cap (not shown), and a final joining of the connector head 10 onto case 12 with a coating of a silicon resin or the like to ensure a final sealed joint between these two elements.

If, however, before the stage of final joining, the operator discovers a defect, in particular a defective welding, it is possible—in a manner characteristic of the present invention—to separate the connector head 10 from the case 12 in order to re-work the defective part, or to exchange the defective part for a non-defective part. More precisely, the separation is carried out by an extraction of clamp 24, simply by gripping the central part 26 of clamp 24 and pulling it out through slot 22. A notch 34 (FIG. 2) allows the easy introduction of the nose of a pliers (or similar tool) to grasp clamp 24. The feed-through lead 14 extending from insulating traverse 16 can then be cut at the welding, and the head 10 then can be withdrawn.

A second welding of the same feed-through leads on a new terminal then will be possible, since a sufficient length of feed-through leads and a sufficient surface for welding the leads to the terminals are provided to be able to perform at least a second welding.

FIGS. 5 and 6 illustrate a second embodiment of the invention, in which the mechanical connection component is one or more pins 36 (two are shown) inserted into corresponding apertures 22 which comprise homologous holes 38 through connector head 10. The holes 38 emerge in front of a groove 40 formed in the side face of the traverse 16. This groove 40 is formed, as in the case of groove 30 of the first embodiment, as a surface feature having a complementary profile to that of the pins 36, in this case a concave circular profile whose radius corresponds to that of cylindrical pins 36. It should be understood that noncylindrical pins and other matching surface shapes could be used.

In this second embodiment, the solidarisation of the connector head to the case is made by depression (arrows 42) of the pins 36 in the holes 38. The separation of the head 10 then can be carried out by an extraction of the pins, for example, by pushing them using an opening (not shown) located in head 10 opposite to holes 38 and having a smaller diameter than holes 38 (holes 38 being emerging holes) and pins 36, thus assuring that pins 36 can be pressed fully into head 10 but not through it when pins 36 are inserted, and removed using a suitable tool.

It will be noted that, in this second embodiment, as well as in the first embodiment, the mechanical fixing of the head 10 to the case 12 does not require a complementary part fixed on the case 12: In this case, the mechanical connection component (clamp 24 or pins 36) instead engages directly on a homologous groove realized on the insulating traverse 16.

This additional function of the traverse (namely, contributing to the mechanical solidarisation) is very economical, since it makes it possible to reduce the number of parts and intermediate times of assembly, for a negligible additional cost of machining the traverse 16, because the groove 30 or 40 being a simple structural form machined in the traverse 16.

Advantageously, the connector head of the present invention thus provides for the possibility of separating the connector head and the case when the head is discovered to be defective, so that a non-defective head can be connected to a non-defective case (or vice versa). This also permits extracting a defective part and carrying out a reworking on the connector head, as appropriate.

One skilled in the art will appreciate the present invention can be practiced by other than the embodiments disclosed, which are presented for purposes of illustration and not of limitation.

We claim:

1. An active implantable medical device such as a pacemaker, defibrillator and/or cardiovertor, comprising:
   a case comprising a face having at least one emerging conducting feed-through lead, and at least one insulating traverse extending out of said face bearing said feed-through conductor leads;
   a connector head made of a rigid insulating material, able to receive the insulating traverse and the electrical contact terminals and having an aperture; and
   a mechanical connection component able to fit in said connector head aperture and engage said at least one insulating traverse to solidarize the case with the connector head, said connection component being a removable component able to allow the separation of the connector head from the case.

2. The device of claim 1, wherein at least one insulating traverse comprises at least one surface feature able to cooperate with the mechanical connection component, said surface feature having a form homologous with the connection component at the point of engagement.

3. The device of claim 2, wherein the surface feature comprises a peripheral groove.

4. The device of claim 2, wherein the mechanical connection component comprises an elastically deformable component able to cooperate with said surface feature by a click-and-ratchet engagement.

5. The device of claim 4, wherein the elastically deformable component is a clamp having a center portion and two opposite ends, and wherein said case further comprises at least two insulating traverses bearing said feed-through conductor leads, and said clamp engages said at least two of said insulating traverses.

6. The device of claim 1, wherein the mechanical connection component further comprises a rigid component able to engage removably said insulating traverse.

7. The device of claim 6, wherein the mechanical connection component further comprises a pin able to cooperate with a surface feature of said insulating traverse, and said aperture further comprises a hole for receiving said pin, said insulating traverse surface feature having a groove shape homologous with the pin.

8. An active implantable medical device such as a pacemaker, defibrillator and/or cardiovertor, comprising:
   a case comprising a face having at least one emerging conducting feed-through lead, and at least one insulating traverse extending out of said face bearing said feed-through conductor leads;
   a connector head made of a rigid insulating material, able to receive the insulating traverse and the electrical contact terminals and having an aperture; and
   a mechanical connection component able to fit in said connector head aperture and engage said at least one insulating traverse to solidarize the case with the connector head, said connection component being a removable component able to allow the separation of the connector head from the case;
   wherein said at least one insulating traverse comprises at least one surface feature able to cooperate with the mechanical connection component, said surface feature having a form homologous with the connection component at the point of engagement; and
   wherein the mechanical connection component comprises an elastically deformable component able to cooperate with said surface feature by a click-and-ratchet engagement.

9. The device of claim 8, wherein the elastically deformable component is a clamp having a center portion and two opposite ends, and wherein said case further comprises at least two insulating traverses bearing said feed-through conductor leads, and said clamp engages said at least two of said insulating traverses.

* * * * *

UNITED STATES PATENT AND TRADEMARK OFFICE
CERTIFICATE OF CORRECTION

PATENT NO. : 6,574,508 B2
DATED : June 3, 2003
INVENTOR(S) : Mounir Zaouali et al.

It is certified that error appears in the above-identified patent and that said Letters Patent is hereby corrected as shown below:

Column 5,
Line 16, before "traverse" insert -- insulating --; and

Column 6,
Line 44, delete "aperture and" and insert -- aperture -- therefor.

Signed and Sealed this

Fifth Day of April, 2005

JON W. DUDAS
*Director of the United States Patent and Trademark Office*